United States Patent

Vega-Noverola et al.

[11] Patent Number: 4,772,618
[45] Date of Patent: Sep. 20, 1988

[54] BENZAMIDES

[75] Inventors: Armando Vega-Noverola; Jose M. Prieto-Soto; Fernando Pujol-Noguera; Jacinto Moragues-Mauri, all of Barcelona; Robert G. W. Spickett, Tibidabo, all of Spain

[73] Assignee: Fordonal, S.A., Madrid, Spain

[21] Appl. No.: 890,946

[22] Filed: Jul. 31, 1986

[30] Foreign Application Priority Data

Aug. 6, 1985 [GB] United Kingdom ............. 8519707

[51] Int. Cl.⁴ ............. A61K 31/395; C07D 405/06; C07D 405/14; C07D 417/06
[52] U.S. Cl. ............. 514/326; 546/207; 546/212; 546/213; 546/214
[58] Field of Search ............. 546/214, 207, 212, 213; 514/326

[56] References Cited

FOREIGN PATENT DOCUMENTS 76530 4/1983 European Pat. Off. ............. 514/326
1507462 4/1978 United Kingdom ............. 514/326

OTHER PUBLICATIONS

Chemical Abstracts, vol. 102, (1985), Item 149, 116, abstracting European Patent Application EP 121,972, published 17 Oct. 1984.
Chemical Abstracts, vol. 99 (1983), Item 194,812d, abstracting European Patent Application EP 76,530, published 13 Apr. 1983.

Primary Examiner—Robert T. Bond
Attorney, Agent, or Firm—Spencer & Frank

[57] ABSTRACT

Substituted benzamides of the general formula I

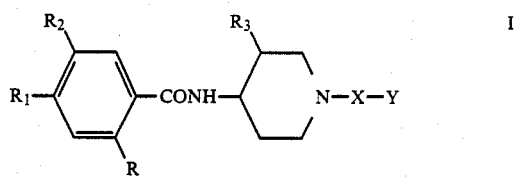

in which:
R represents an alkoxy, alkenyloxy or alkynyloxy group containing up to 7 carbon atoms in the group,
$R_1$ is hydrogen or a $NR_4R_5$, or $NR_6COR_7$ group, where $R_4$, $R_5$ and $R_6$, which may be the same or different, is each hydrogen or an alkyl group and $R_7$ is an alkyl or trifluoromethyl group,
$R_2$ is hydrogen, halogen, or a nitro, or sulphamoyl group,
$R_3$ represents hydrogen or a methyl or methoxy group,
X represents a hydrocarbon chain containing 1 to 4 carbon atoms, one of which may optionally be replaced by an oxygen atom,
Y represents a non-aromatic cyclic ether or a non-aromatic cyclic thioether group and pharmaceutically acceptable salts thereof are useful in the treatment of gastro-intestinal disorders. Various methods of synthesis are described including synthesis via novel amines of the formula

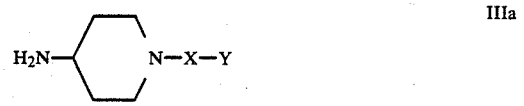

which are themselves obtained by reduction of the corresponding oximes.

22 Claims, No Drawings

BENZAMIDES

DESCRIPTION

This invention relates to N-heterocyclic substituted benzamides, methods for their preparation, compositions containing them and their use in medical treatment.

Substituted benamides have been shown to possess a number of pharmacological properties most of which are related to their ability to antagonise the central and peripheral effects of dopamine and/or facilitate the release of acetylcholine onto muscarinic receptors in the gastrointestinal smooth muscle. This has led to their successful clinical use as antiemetic and in the treatment of a wide range of gastrointestinal disorders of somatic, psychosomatic and iatrogenic origin.

Nevertheless, blockade of dopamine receptors in the striatum and hypophysis has been associated with the occurrence of extrapyramidal symptoms and hyperprolactinemia related side effects in some patients treated with benzamide drugs such as metoclopramide and clebopride, which limits their overall usefulness.

We have now found that the introduction of various cyclic ethers or thioethers onto the ring nitrogen atom of N-4-piperidyl series of benzamides results in compounds, which while maintaining the desired gastrokinetic activity, have a significantly reduced antidopaminergic activity.

Accordingly, the present invention provides a compound of the formula:

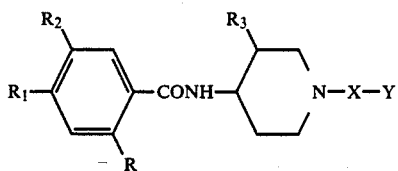

in which:
R represents an alkoxy, alkenyloxy or alkynyloxy group containing up to 7 carbon atoms in the group, $R_1$ is hydrogen or a $NR_4R_5$, or $NR_6COR_7$ group, where $R_4$, $R_5$ and $R_6$, which may be the same or different, is each hydrogen or an alkyl group and $R_7$ is an alkyl or trifluoromethyl group, $R_2$ is hydrogen, halogen, or a nitro, or sulphamoyl group, $R_3$ represents hydrogen or a methyl or methoxy group, X represents a hydrocarbon chain containing 1 to 4 carbon atoms, one of which may optionally be replaced by an oxygen atom, Y represents a non-aromatic cyclic ether or a non-aromatic cyclic thioether group and pharmaceutically acceptable salts thereof.

The alkyl of alkoxy groups mentioned in relation to the groups $R_1$–$R_7$ in compounds of the invention are usually "lower" alkyl or alkoxy, that is containing up to 6 and particularly up to 4 carbon atoms, the hydrocarbon chain being branched or straight.

In the compounds of the invention, Y represents a non-aromatic cyclic ether group or non-aromatic cyclic thioether group. This means that Y contains no aromatic ring systems but contains at least one ring system having at least two ring carbon atoms and one or more ring oxygen or ring sulphur atoms. The ring system may be a mononuclear ring containing at least three ring atoms or a spiro ring or a fused or non-fused binuclear or polynuclear ring system. Such spiro or other bi or polynuclear ring systems will contain at least six ring atoms. Mononuclear rings containing five to eight ring atoms of which at least one is oxygen or sulphur and the remaining ring atoms normally being carbon are of particular importance. These cyclic ether or thioether ring systems may also contain more than one ring oxygen and/or sulphur atom and when more than one ring oxygen and/or sulphur atom is present, they are in non-adjacent positions in the ring. The cyclic ether or thioether ring system may contain double bonds provided that the double bonds do not form part of an aromatic ring system. When the cyclic ether or thioether ring system contains a further ring system in addition to the cyclic ether or thioether ring, the further ring system may be a non-aromatic carbocyclic ring system or a non-aromatic heterocyclic ring system including a further cyclic ether or thioether ring and the further ring system may be linked to the first cyclic ether or thioether ring by fusion or by a direct bond or via a bivalent linking group such as a methylene or $C_2$–$C_6$ polymethylene group.

When the cyclic ether or thioether ring system includes a further ring system, it is preferred that the cyclic ether or thioether ring is directly bonded to the group X in formula I.

The cyclic ether or thioether ring system may be substituted by alkyl, alkoxy or alkoxyalkyl substituents. When such substituents are present, it is preferred that the alkyl groups or the alkyl residues in the alkoxy or alkoxyalkyl groups contain 1 to 6 carbon atoms and reference here may be made to methyl, methoxy or methoxymethyl substitution particularly.

Typical cyclic ethers of thioethers which may be present as group Y in the compounds of the invention are the following:

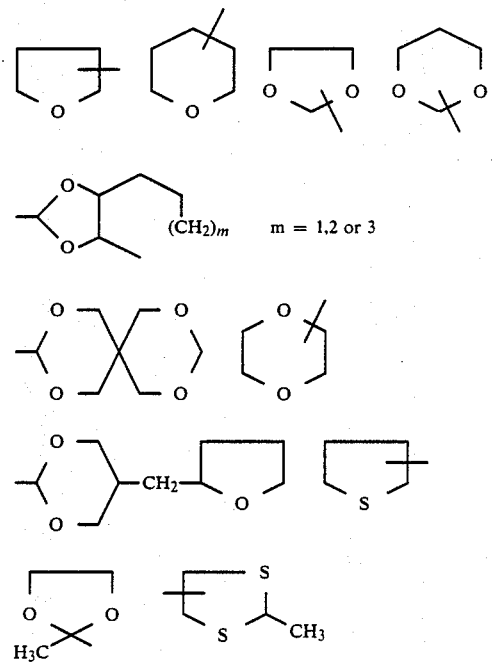

The group X in the compounds of the present invention contains a straight or branched hydrocarbon chain of 1 to 4 atoms. It is preferred that this chain be a methylene or polymethylene chain but when a polymethylene chain is present, one of the methylene groups may be replaced by an ether oxygen. When the group X is to be branched, the group X can be, for example, a methylpropylene or ethylethylene group. While it is normally the case that the group X will be saturated, it is also possible for the group to contain one site of carbon-to-carbon unsaturation, e.g. an olefinic double bond.

The benzamide residue in the molecule will be one having an ether group at position 2. This is the group R. R will normally contain up to 7 carbon atoms and it is preferred that R be a straight or branched alkoxy group. When R is an alkoxy group, it is preferred that the group contains up to 6 carbon atoms since it has been found that this group can significantly influence the anti-dopaminergic activity of the compound. R can therefore be an alkoxy group such as methoxy, ethoxy, n-propoxy, n-butoxy, n-pentoxy or n-hexoxy.

Group R may also represent an unsaturated ether group e.g. alkenyloxy or alkynyloxy, and in such cases, it is preferred that the unsaturated group, which may be straight or branched, contains 2 to 6 carbon atoms, e.g. allyloxy or propargyloxy.

The group R may be the only substituent present on the benzamide residue. However, it is preferred that the benzamide residue be disubstituted or, usually better still, trisubstituted. In this case, the group $R_2$ may represent halogen, for example bromine or fluorine but particularly chlorine, or may represent nitro. Alternatively, $R_2$ can represent a sulphamoyl group while optionally can be N-substituted or can be substituted by one or two alkyl groups each containing up to 6 carbon atoms, e.g. N-ethyl or N,N-diethyl sulphamoyl.

The group $R_1$ is preferably an amino group, or an N-alkylamino or N,N-dialkylamino group where each alkyl group contains 1 to 6 carbon atoms or an acylamino residue where the acyl group is an alkanoyl group of 1 to 6 carbon atoms, particularly an acetyl group or a trifluoroacetyl group.

The invention also provides salts of compounds of structures (I), with biologically and pharmacologically acceptable inorganic and organic acids, non-limiting examples of which are sulphates, hydrohalide salts, phosphates, $C_1$-$C_6$ alkane sulphonates, arylsulphonates, salts of aliphatic or aromatic acids containing 1-20 carbon atoms and which may contain one or more double bonds or other functional groups such as hydroxy, alkoxy, amino, or keto. Also included within the scope of the invention are pharmaceutically acceptable quaternary ammonium salts of compounds of general formula I in which the tertiary nitrogen atom of the piperidine ring is quaternised by reaction for example with a $C_1$-$C_6$ alkyl halide or sulphate.

According to a feature of the present invention, the compounds of the invention are prepared by the process which comprises reacting a reactive derivative of a benzoic acid of the general formula:

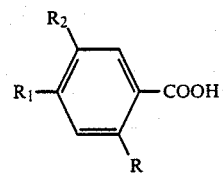

II (wherein R, $R_1$ and $R_2$ are as hereinbefore defined) with a piperidine derivative of the general formula III:

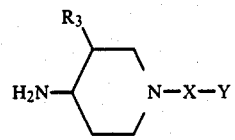

III wheren $R_3$, X and Y are as hereinbefore defined. The reactive derivative of the said benzoic acid may be a halide (preferably chloride), an alkyl ester (preferably methyl ester), an anhydride or a mixed anhydride.

The reaction is preferably carried out in the presence of an inert organic solvent, for example benzene, toluene, chloroform, tetrahydrofuran, N,N-dimethylformamide or dioxan, at a temperature between $-5°$ and $120°$ C.

Halides of the benzoic acids of general formula II can be prepared by reaction of the acid with thionyl chloride of a phosphorus halide in the presence of an inert organic solvent such as benzene, toluene or a halogenated hydrocarbon. Mixed anhydrides of the benzoic acids of general formula II can be prepared by the reaction of the acid with, for example, an alkyl chloroformate in the presence of an organic nitrogen-containing base, e.g. triethylamine, in an inert organic solvent, e.g. tretrahydrofuran, N,N-dimethylformamide or methylene chloride and at a temperature between $-20°$ and $+25°$ C. Esters and anhydrides of the benzoic acids of formula II, which may be employed as starting materials in the aforementioned process, can be prepared from the benzoic acids by methods known per se.

In the preparation of those compounds of general formula I wherein the symbol $R_1$ represents an amino group, it is sometimes advisable to use as starting material corresponding compounds in which the amino group is protected by an acyl group, the acyl protecting group preferably being acetyl, chloroacetyl, trifluoroacetyl or phthaloyl. After the reaction the N-acylated intermediate products are subjected to alkaline hydrolysis to give the corresponding compounds of general formula I in which $R_1$ represents an amino group. Alkaline hydrolysis of the N-acylated compound is preferably carried out at a temperature between $20°$ and $90°$ C. with sodium or potassium hydroxide in an aqueous-alcoholic solution. The compounds of the invention, in which $R_2$ is as defined above but other than a nitro group can also be prepared from an N-unsubstituted compound of formula IV:

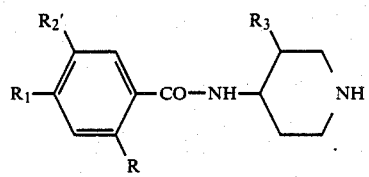

IV wherein, $R_2'$ is as defined above for $R_2$ but other than a nitro group and R, $R_1$ and $R_3$ are as hereinbefore defined.

The compound IV is prepared by subjecting the corresponding N-benzyl compound to catalytic hydrogenolysis in a solvent such as a $C_1$–$C_6$ alcohol in the presence of a noble metal catalyst, e.g. palladium or platinum, which may be absorbed on an inert support such as carbon or barium sulphate, in the presence of hydrogen at normal or elevated pressure and at temperatures between ambient and 100° C. The compound IV can also be prepared from an ethoxycarbonyl compound of formula V:

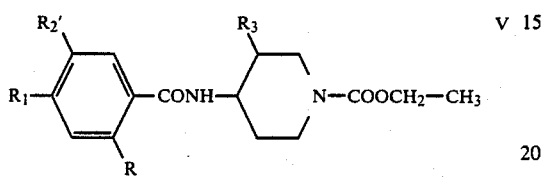
V (wherein R, $R_1$, $R_2'$, and $R_3$ are as hereinbefore defined) by hydrolysis with sodium or potassium hydroxide in an organic solvent, for example ethanol or isopropanol, at the boiling point of the solvent. The compound IV may then be reacted with an appropriate halide or sulphonate of structure:

W—X—Y          VI where W is a halogen atom or a methanesulphonate, p-toluenesulphonate or benzenesulphonate group and X and Y are as defined above in the presence of a base such as sodium or potassium carbonate or sodium or potassium bicarbonate, in an organic solvent such as toluene, dioxane or methyl isobutyl ketone at a temperature between 40° and 140° C.

The compounds of the invention of formula I can also be prepared by methods which include the formation of the cyclic ether or cyclic thioether in the last step of synthesis. More specifically, compounds of formula I can be prepared from the corresponding hydroxy- or -thio-derviatives of formula VII:

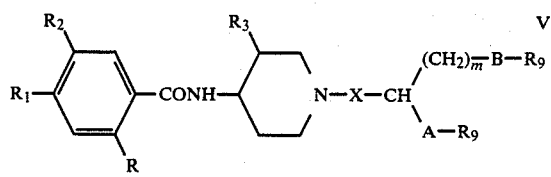
VII wherein A and B which may be the same of different, is each an oxygen or sulphur atom, m is 0, 1, 2, 3 or 4, $R_9$ is hydrogen or a $C_1$–$C_6$ alkyl group and R, $R_1$, $R_2$, $R_3$ and X are as hereinbefore defined. The compound VII is cyclized with a dehydrating agent, a dihydroxy compound or an aldehyde in the presence of a solvent such as benzene or toluene at elevated temperatures e.g. the boiling point of the solvent.

The compounds of general formula I can also be prepared, according to a further feature of the invention, by the direct reaction of a benzoic acid of general formula II with a piperidine derivative of general formula III in the presence of an appropriate dehydrating agent. Such agents include silicon tetrachloride, a mono-, di- or trialkyl-silyl chloride, titanium tetrachloride, N,N'-dicyclohexyl-carbodiimide, carbonyl diimidazole, thionyl chloride, sulphur trioxide in dimethyl sulphoxide, toluene-p-sulphonyl chloride, acetone dimethyl acetal or a polymeric dehydrating agent. The reaction can be carried out in an inert organic solvent, e.g. methylene chloride, acetone, pyridine, ethyl acetate or dioxan, at a temperature between 20° and 110° C.

The compounds of the invention of formula I can also be prepared from the hydroxy derivative of formula VIII:

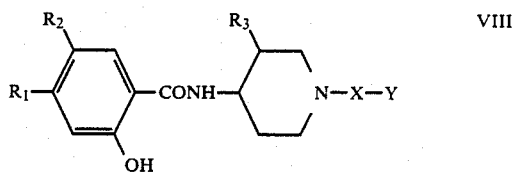
VIII wherein $R_1$, $R_2$, $R_3$, X and Y are as hereinbefore defined, by reaction with a halogen derivative of formula IX.

Z—R          IX wherein Z is chloro, bromo or iodo and R is as hereinbefore defined. The reaction can be carried out in an organic solvent such as methyl isobutyl ketone, toluene, dioxane, or toluene at a temperature between 40° and 140° C. and in the presence of an organic or inorganic base such as sodium or potassium carbonate.

The intermediate amines of formula III wherein $R_3$ is hydrogen, are themselves new compounds and form a further aspect of the present invention. These compounds of formula III wherein $R_3$ is hydrogen, can be prepared by the reduction of the corresponding oxime of the formula X:

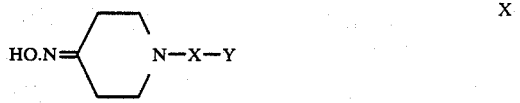
X (wherein X, and Y are as hereinbefore defined) with lithium aluminium hydride in the presence of diethyl ether or tetrahydrofuran at a temperature between 5° and 65° C. Oximes X may be obtained by reacting the 4-piperidoneoxime of formula XI with a halide or sulphonate derivative of formula VI,

XI in the presence of an acid-binding agent such as an alkali metal carbonate or bicarbonate and in an organic solvent such as toluene, dioxane or methyl isobutyl ketone at a temperature between 40° and 140° C.

Oximes X may also be prepared by reacting the corresponding ketone of formula XII:

XII with hydroxylamine by methods known per se.

The intermediates II, used in the preparation of the compounds of the invention are also known compounds and are described, for example, in GB Nos. 1,507,462, 1,088,531 and 1,019,781.

The pharmacological screening of a series of N-heterocyclic substituted benzamide derivatives led to the important demonstration of potent gastrokinetic activity in the absence of dopamine antagonist effects.

The pharmacological screening of compounds to optimise the gastro-intestinal kinetic effects was carried out using the following tests:

1. Stomach emptying in the rat, administering compounds via the oral (0.1-1 mg/Kg) and intraperitoneal routes (1-10 mg/Kg), (see Jacoby, H. I. and Brodie, D. A., Gastroenterol. 52, 676-684, 1967).
A stomach emptying index was calculated as follows:
40 Glass beads (diam≃1 mm) administered to each rat after dosing with the test compounds at 0.1, 0.3 and 1 mg/Kg p.o. Results calculated according to the formulae:

$$R = \frac{n_x - n_c}{40 - n_c} \times 100$$

where:
$n_c$ = the number of beads empited by control animals.
$n_x$ = the number of beads emptied by treated animals.
and:

R = % maximum response.
SEI = Stomach emptying index $$SEI = \frac{R_{(0.1)} + R_{(0.3)} + R_{(1)}}{3}$$

The pharmacological screening for undesirable effects upon central and peripheral $D_2$ ($DA_2$)—dopamine receptors was carried out using the following tests:

2. Apomorphine-induced stereotyped behaviour in the rat, administering compounds via the intraperitoneal route. (see Janssen, P. A. J., Niemegeers, C. J. E. and Jageneau, A. H. Arzneim. Forsch. 10, 1003-1005, 1960).

3. Apomorphine-induced emesis in the dog, administering compounds via the intravenous route, in doses up to 1 mg/Kg i.v. (see Prala, J. J., High, J. P., Hasses, G. L., Burke, J. C. and Craven, B. N., J. Pharmac. Exp. Therap., 127, 55-65, 1959).

Structure activity relationship demonstrated that the substances of formula I retain the potent stomach emptying properties of clebopride but have reduced and in some cases are devoid of antidopaminergic activity when tested at up to 30 mg/Kg intraperitoneally in test 2 above and at up to 1 mg/Kg intravenously in test 3 above.

For example, sample compounds of formula I when tested in tests 1, 2 and 3 above and compared with metoclopramide and clebopride gave results set out in Table 1. For comparative purposes, analogues of invention compounds having aromatic heterocyclic rings were also tested in tests 1, 2 and 3 above and compared with metoclopramide and clebopride and gave results set out in Table 2.

TABLE 1

| COMPOUND (Table after example 2) | STOMACH EMPTYING INDEX IN THE RAT VIA ORAL ROUTE | ANTIDOPAMINERGIC ACTIVITY: RAT STEREOTYPE BEHAVIOUR INDUCED BY APOMORPHINE ID$_{50}$ (mg/kg)ip | ANTIDOPAMINERGIC ACTIVITY DOG EMESIS SCREEN ID$_{50}$ (μg/kg)iv |
|---|---|---|---|
| METOCLOPRAMIDE | 24.7 | 5.4 | 76.7 |
| CLEBOPRIDE | 50.0 | 0.3 | 9.6 |
| COMPOUND 57 | 51.0 | >30.0 | >1000.0 |
| COMPOUND 66 | 53.7 | >30.0 | >1000.0 |
| COMPOUND 109 | 61.3 | >30.0 | >1000.0 |
| COMPOUND 98 | 60.1 | >30.0 | >1000.0 |
| COMPOUND 95 | 49.0 | >30.0 | >1000.0 |
| COMPOUND 91 | 54.9 | >30.0 | >1000.0 |
| COMPOUND 108 | 51.0 | >30.0 | >1000.0 |
| COMPOUND 116 | 56.2 | >30.0 | >1000.0 |
| COMPOUND 39 | 45.8 | >30.0 | >1000.0 |

TABLE 2 with aromatic compounds

| COMPOUND | STOMACH EMPTYING INDEX IN THE RAT VIA ORAL ROUTE | ANTIDOPAMINERGIC ACTIVITY: RAT STEREOTYPE BEHAVIOUR INDUCED BY APOMORPHINE ID$_{50}$ (mg/kg)ip | ANTIDOPAMINERGIC ACTIVITY DOG EMESIS SCREEN ID$_{50}$ (μg/kg)iv |
|---|---|---|---|
| METOCLOPRAMIDE | 24.7 | 5.4 | 76.7 |
| CLEBOPRIDE | 50.0 | 0.3 | 9.6 |
| COMPOUND A | 40.3 | 3-10 | 10-30 |
| COMPOUND B | 17.7 | 10-30 | 30-100 |
| COMPOUND C | 25.0 | 10-30 | 30-100 |

TABLE 2-continued

| | with aromatic compounds | | |
|---|---|---|---|
| COMPOUND | STOMACH EMPTYING INDEX IN THE RAT VIA ORAL ROUTE | ANTIDOPAMINERGIC ACTIVITY: RAT STEREOTYPE BEHAVIOUR INDUCED BY APOMORPHINE $ID_{50}$ (mg/kg)ip | ANTIDOPAMINERGIC ACTIVITY DOG EMESIS SCREEN $ID_{50}$ (µg/kg)iv |
| COMPOUND D | 19.3 | 3–10 | 10–30 |

Clebopride is N(1-benzylpiperid-4-yl)-2-methoxy-4-amino-5-chlorobenzamide.
Metoclopramide is N—[2-(diethylamino)ethyl]-2-methoxy-4-amino-5-chlorobenzamide.
Compound A: N—[1-(2-thienylmethyl)piperid-4-yl]-2-methoxy-4-amino-5-chlorobenzamide.
Compound B: N—[1-(2-thienylmethyl)piperid-4-yl]-2-methoxy-4-amino-5-nitro-benzamide.
Compound C: N—[1-(2-piridylmethyl)piperid-4-yl]-2-methoxy-4-amino-5-chlorobenzamide.
Compound D: N—[1-(2-furylmethyl)piperid-4-yl]-2-methoxy-4-amino-5-chlorobenzamide.

The new compounds therefore represent an important advance over existing therapy in certain disorders of gastro-intestinal motility in that they will be devoid of undesirable side effects associated with dopamine receptor blockade (i.e. extrapyramidal side-effects, increased prolactin secretion etc.) at therapeutic dosage levels.

The present invention also provides pharmaceutical compositions which comprise, as active ingredient, at least one compound of general formula I, or a pharmacologically acceptable salt in association with a pharmaceutically acceptable carrier or diluent. Preferably the compositions are made up in a form suitable for oral, topical, percutaneous or parental administration.

The pharmaceutically acceptable carriers or diluents which are admixed with the active compound, or compounds or salts of such compounds, to form the compositions of this invention are well known per se and the actual excipients used depend inter alia on the intended method of administering the compositions. Compositions of this invention are preferably adapted for administration per os. In this case, the composition for oral administration may take the form of tablets, capsules, lozenges or effervescent granules or liquid preparations, such as mixtures, elixirs, syrups or suspensions, all containing one or more compounds of the invention; such preparations may be made by methods well known in the art.

The diluents which may be used in the preparation of the compositions include those liquid and solid diluents which are compatible with the active ingredient, together with colouring or flavouring agents, if desired. Tablets or capsules may conveniently contain between 1 and 20 mg of active ingredient or the equivalent amount of an acid addition salt thereof.

The liquid compositions adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in water or an appropriate parenteral injection fluid.

A further aspect of the present invention provides a method of treating various gastro-intestinal disorders including vomiting in mammals including man by administering an effective amount of a compound or salt of formula I, suitably using compositions and administration routes described above. Effective doses are normally in the range of 1–100 mg of active ingredient per day.

In another aspect of the invention, the compounds may be mixed with active anti-acid and anti-ulcer agents (excluding anti-cholinergic agents) for oral or, in appropriate cases, for parenteral use.

The following Reference Example and Examples illustrate the preparation of compounds of the present invention.

REFERENCE EXAMPLE

A mixture of piperid-4-one oxime (46 g; 0.04 moles), 2-tetrahydrofurylmethyl methanesulphonate (79.3 g; 0.44 moles) and anhydrous potassium carbonate (56.5 g; 0.40 moles) in methyl isobutyl ketone (625 ml), was boiled under reflux with stirring for 48 hours. After cooling, the reaction mixture was washed with brine, dried ($Na_2SO_4$), and the solvent removed in vacuo. The residue was crystallised from diisopropyl ether to give 1-(2-tetrahydrofurylmethyl)-piperid-4-one oxime (42.5 g), m.p. 104°–106°.

A solution of 1-(2-tetrahydrofurylmethyl)piperid-4-one oxime (42.5 g; 0.22 moles) in anhydrous tetrahydrofuran (700 ml) was added dropwise to a suspension of lithium aluminium hydride (24.4 g; 0.64 moles) in anhydrous tetrahydrofuran (300 ml). The reaction mixture was left with stirring at room temperature overnight and then, water (24.5 ml), 4N sodium hydroxide aqueous solution (24.5 ml) and water (73.5 ml) were successively added, filtered, the filtrates dried ($Na_2SO_4$) and brought to dryness in vacuo. The resulting oil (28 g) was distilled to give 1-(2-tetrahydrofurylmethyl)-4-aminopiperidine, boiling point 94°–98° C./0.2 mm Hg.

Also prepared in a similar manner, using approximate oximes as starting materials, were the compounds of the following Table:

| R | Boiling point/mm Hg |
|---|---|
| $CH_2$—$CH_2$—(tetrahydrofuran-2-yl) | 108–112° C./0.25 |
| $CH_2$—$CH_2$—$CH_2$—(tetrahydrofuran-2-yl) | 117–119° C./0.1 |

-continued

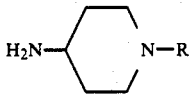

| R | Boiling point/mm Hg |
|---|---|
| (THF-CH₂-O-CH₂CH₂–) | 138–143° C./0.4 |
| (oxetane-CH₂–) | 92–95° C./0.05 |
| (tetrahydropyran-CH₂–) | 110–114° C./0.15 |
| (1,3-dioxolane-2-CH₂–) | 104–107° C./0.2 |
| (1,3-dioxane-2-CH₂–) | 121–126° C./0.4 |
| (1,3-dioxolane-CH₂–) | 63–65° C./0.1 |
| (4,5-dimethyl-1,3-dioxolan-2-yl-CH₂–) | 107–114° C./0.1 |
| (1,3-dioxolan-2-yl-CH₂-CH(THF)-) | 183–190° C./0.1 |
| (2,2-dimethyl-1,3-dioxolan-4-yl-CH₂–) | 80–82° C./0.2 |

EXAMPLE 1

Triethylamine (5.6 ml; 0.04 moles) and ethyl chloroformate (3.84 ml; 0.04 moles) were added successively to a stirred suspension of 2-ethoxy-4-amino5-chlorobenzoic acid (8.6 g; 0.04 moles) in anhydrous tetrahydrofuran (300 ml) whilst maintaining the temperature between −5° and −10° C. After stirring at this temperature for 0.5 hours, a solution of 1-(2-tetrahydrofurylmethyl)-4-aminopiperidine (8.0 g; 0.04 moles) in anhydrous tetrahydrofuran (50 ml) was added, the temperature was maintained at −5° to −10° C. for 1 hour and then allowed overnight to reach room temperature. The solvent of the mixture was removed in vacuo, the residue poured into water, extracted with chloroform and the organic layers washed with water. The chloroformic solution was dried (Na₂SO₄) and the solvent removed in vacuo to give an oil which was treated with the stoichiometric amount of fumaric acid in boiling absolute ethanol. N-[1-(2-Tetrahydrofurylmethyl)-piperid-4-yl]-2-ethoxy-4-amino-5-chlorobenzamide hydrogen fumarate (10.6 g) was thus obtained, m.p. 199°–201° C. (d).

EXAMPLE 2

A mixture of N-(piperid-4-yl)-2-methoxy-4-amino-5-chlorobenzamide (2.8 g; 0.010 moles), 2-(2-chloroethyl)-1,3-dioxane (1.65 g; 0.011 moles) and anhydrous potassium carbonate (1.4 g; 0.010 moles) in methyl isobutyl ketone (125 ml) was boiled under reflux with stirring for 96 hours. The reaction mixture was cooled, washed with water, dried (Na₂SO₄) and the solvent removed in vacuo to give an oily residue which was treated with the stoichiometric amount of fumaric acid in boiling absolute ethanol. After cooling N-[1-[2-(1,3-dioxonyl)ethyl]-piperid-4-yl]-2-methoxy-4-amino-5-chlorobenzamide hydrogen fumarate (2.1 g) m.p. 223°–225° C. (d) was obtained.

The compounds of general formula I included in the following Table were prepared according to the processes disclosed in Examples 1 or 2 as indicated.

| NO. | Y | X | R (*) | R₁ | R₂ | R₃ | Method Example | Base/Salt form (**) | m.p. °C. |
|---|---|---|---|---|---|---|---|---|---|
| 1 | tetrahydrofuran-2-yl | CH₂ | OCH₃ | H | H | H | 1 | C₄H₄O₄ | 144-146 |
| 2 | " | " | H | " | " | " | " | Base | 132-134 |
| 3 | " | " | " | " | Cl | " | " | C₄H₄O₄ | 199-201 |
| 4 | " | " | OCH₃ | 4-NH₂ | NO₂ | " | " | Base | 199-201 |
| 5 | " | " | " | " | H | " | " | 2C₄H₄O₄ | 171-173 |
| 6 | " | " | " | H | NO₂ | " | " | ½C₄H₄O₄ | 225-227 |
| 7 | " | " | " | " | SO₂NH₂ | " | " | C₄H₄O₄ | 194-196 |
| 8 | " | " | " | 4-AcNH | H | " | " | " | 168-170 |
| 9 | " | " | " | H | Cl | " | " | Base | 93-95 |
| 10 | " | " | " | 4-NH₂ | " | " | " | C₄H₄O₄ | 191-193 |
| 11 | " | " | " | 4-AcNH | " | " | " | " | 160-162 |
| 12 | " | " | OCH₂—CH=CH₂ | 4-Ac(CH₃)N | " | " | " | Base ½H₂O | 61-63 |
| 13 | " | " | OCH₂CH=CH—CH₃ | 4-NH₂ | " | " | " | C₄H₄O₄ | 183-185 |
| 14 | " | " | OCH₂—CH=C(CH₃)₂ | 4-AcNH | " | " | " | " | 165-167 |
| 15 | " | " | " | 4-NH₂ | " | " | " | " | 185-187 |
| 16 | " | " | OCH₂—CH=C(CH₃)₂ | " | " | " | " | " | 172-174 |
| 17 | " | " | OC₂H₅ | " | " | " | " | " | 199-201 |
| 18 | " | " | OC₃H₇ | " | " | " | " | " | 198-200 |
| 19 | " | " | OC₄H₉ | " | " | " | " | " | 185-188 |
| 20 | " | " | OC₅H₁₁ | " | " | " | " | " | 194-196 |
| 21 | " | " | OC₆H₁₃ | " | " | " | " | " | 181-183 |
| 22 | " | " | OC₇H₁₅ | " | " | " | " | " | 171-173 |
| 23 | " | " | OCH₂—C≡CH | " | " | " | " | " | 140-143 |
| 24 | " | " | OCH₃ | " | NO₂ | " | " | C₄H₄O₄ | 202-204 |
| 25 | " | " | " | 4-AcNH | " | " | " | " | 181-183 |
| 26 | " | " | OCH₂—CH=CH₂ | 4-NH₂ | " | " | " | " | 198-200 |
| 27 | " | " | OCH₂—C≡CH | " | " | " | " | " | 137-140 |
| 28 | " | " | OC₄H₉ | " | " | " | " | Base | 142-144 |
| 29 | " | " | OCH₃ | " | Cl | CH₃ | " | " | 147-150 |
| 30 | " | " | " | " | NO₂ | OCH₃ | " | " | 175-177 |
| 31 | " | " | " | " | Cl | " | " | " | 144-146 |
| 32 | " | " | OC₄H₉ | " | " | " | " | " | 277-280 |
| 33 | " | CH₂—CH₂ | OCH₃ | " | " | H | 2 | C₄H₄O₄ | 219-221 |

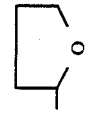

-continued structure: R2, R1, R3 on phenyl ring with CONH-[piperidine]-N-X-Y

| NO. | Y | X | R (*) | R₁ | R₂ | R₃ | Method Example | Base/Salt form | m.p. °C |
|---|---|---|---|---|---|---|---|---|---|
| 34 | " | " | OC₄H₉ | " | NO₂ | " | 1 | Base | 219–220 |
| 35 | " | " | OCH₂—CH=CH₂ | " | Cl | " | " | C₄H₄O₄ | 213–215 |
| 36 | " | " | OCH₂—CH=CH—CH₃ | " | " | " | " | " | 174–177 |
| 37 | " | " | OC₂H₅ | " | " | " | " | " | 188–190 |
| 38 | " | (CH₂)₃ | OC₃H₇ | " | " | " | " | " | 183–185 |
| 39 | " | " | OC₄H₉ | " | " | " | " | " | 205–207 |
| 40 | " | " | OC₆H₁₃ | " | " | " | " | " | 213–215 |
| 41 | " | " | OCH₂—CH=CH₂ | " | " | " | " | " | 186–188 |
| 42 | " | " | OCH₂—CH=CH—CH₃ | " | " | " | " | " | 176–178 |
| 43 | " | " | OCH₃ | " | " | " | " | " | 193–195 |
| 44 | " | (CH₂)₂—O—CH₂ | OC₃H₇ | " | " | " | " | " | 160–162 |
| 45 | " | " | OC₄H₉ | " | " | " | " | " | 162–164 |
| 46 | " | " | OCH₂—CH=CH₂ | " | " | " | " | " | 156–158 |
| 47 | " | " | OCH₂—C≡CH | " | " | " | " | " | 154–156 |
| 48 | " | " | OCH₂—CH=CH—CH₃ | " | " | " | " | " | 127–129 |
| 49 | " | CH₂ | OCH₃ | " | " | " | 2 | C₄H₄O₄ | 159–161 |
| 50 | " | " | OC₃H₇ | " | " | " | " | " | 221–223 |
| 51 | " | " | OC₄H₉ | " | " | " | " | Base | 141–143 |
| 52 | " | " | OCH₃ | " | NO₂ | " | " | " | 146–148 |
| 53 | " | " | " | " | Cl | " | " | " | 229–231 |
| 54 | 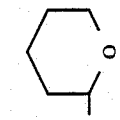 | " | " | " | " | " | " | C₄H₄O₄ | 208–210 |
| 55 | " | " | OC₂H₅ | " | " | " | 1 | " | 203–205 |
| 56 | " | " | OC₃H₇ | " | " | " | " | " | 217–219 |
| 57 | " | " | OC₄H₉ | " | " | " | " | " | 214–216 |
| 58 | " | " | OCH₂CH=CH₂ | " | " | " | " | " | 192–194 |
| 59 | " | " | OCH₂C≡CH | " | " | " | " | " | 184–186 |
| 60 | " | " | OCH₂—CH=CH—CH₃ | " | " | " | " | " | 184–186 |
| 61 | " | " | OCH₃ | " | NO₂ | " | " | Base | 224–226 |
| 62 | " | " | " | 4-AcNH | Cl | " | " | C₄H₄O₄ | 182–184 |
| 63 | " | " | " | 4-NH₄ | " | " | 2 | Base | 207–209 |
| 64 | 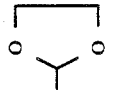 | " | OC₂H₅ | " | " | " | 1 | C₄H₄O₄ | 193–195 |

-continued

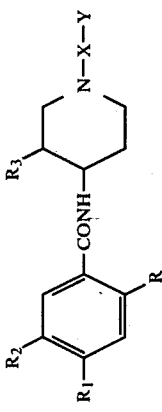

| NO. | Y | X | R (*) | R₁ | R₂ | R₃ | Method Example | Base/Salt form | m.p. °C. |
|---|---|---|---|---|---|---|---|---|---|
| 65 | | " | OC₃H₇ | " | " | " | " | ½C₄H₄O₄ | 177–180 |
| 66 | | " | OC₄H₉ | " | " | " | " | C₄H₄O₄ | 172–174 |
| 67 | | " | OC₅H₁₁ | " | " | " | " | " | 164–166 |
| 68 | | " | OC₆H₁₃ | " | " | " | " | " | 179–181 |
| 69 | | " | OC₇H₁₅ | " | " | " | " | " | 144–146 |
| 70 | | " | OCH₂—CH=CH₂ | " | " | " | " | " | 168–170 |
| 71 | | " | OCH₂—C≡CH | " | " | " | " | " | 173–175 |
| 72 | | " | OCH₂—CH=CH—CH₃ | " | " | " | " | " | 158–160 |
| 73 | | " | OCH₃ | 4-AcNH | " | " | " | C₄H₄O₄ | 176–178 |
| 74 | | " | OCH₂—CH=CH₂ | " | " | " | " | " | 143–146 |
| 75 | | " | OC₄H₉ | 4-CH₃—NH | " | " | " | " | 169–171 |
| 76 | | " | " | 4-NH₂ | NO₂ | " | " | Base | 176–178 |
| 77 | | " | OCH₃ | " | " | " | " | ½C₄H₄O₄ | 200–202 |
| 78 | | " | OC₂H₅ | 4-N(CH₃)₂ | Cl | " | " | C₄H₄O₄ | 114–117 |
| 79 | | " | OCH₃ | 4-NH₂ | " | CH₃ | 2 | Base | 139–141 |
| 80 | | " | OC₄H₉ | " | " | OCH₃ | " | C₄H₄O₄ | 172–174 |
| 81 | | " | OCH₃ | " | " | H | 1 | " | 193–195 |
| 82 | | " | OC₂H₅ | " | " | " | " | " | 187–189 |
| 83 | | " | OC₃H₇ | " | " | " | " | " | 153–155 |
| 84 | | " | OC₄H₉ | " | " | " | " | " | 153–155 |
| 85 | | " | OCH₃ | " | " | " | " | C₄H₄O₄ | 207–209 |
| 86 | | " | OC₂H₅ | " | " | " | " | Base | 166–168 |
| 87 | | " | OC₃H₇ | " | NO₂ | " | " | C₄H₄O₄ | 163–165 |
| 88 | | " | OC₄H₉ | " | " | " | " | Base | 181–183 |
| 89 | | " | OCH₃ | " | " | " | " | " | 215–217 |

-continued

Structure: R2, R1, R3 substituted benzene with CONH linked to piperidine ring (N–X–Y)

| NO. | Y | X | R (*) | R1 | R2 | R3 | Method Example | Base/Salt form | m.p. °C |
|-----|---|---|-------|----|----|----|----------------|----------------|---------|
| 90 | 4,4,5,5-tetramethyl-1,3-dioxolan-2-yl | " | " | " | Cl | " | 2 | " | 178–180 |
| 91 | " | " | $OC_4H_9$ | " | " | " | " | " | 185–187 |
| 92 | 4-(methoxymethyl)-1,3-dioxolan-2-yl | " | $OCH_3$ | " | " | " | " | " | 145–147 |
| 93 | 2-(1,3-dioxolan-2-yl)methyl (CH2–O–CH3 substituted) | " | $OC_4H_9$ | " | " | " | " | Base | 178–180 |
| 94 | 2-methyl-hexahydro-1,3-benzodioxole (H) | " | $OCH_3$ | " | " | " | " | " | 183–185 |
| 95 | 2-methyl-1,3-dioxolan-2-yl | " | $OC_4H_9$ | " | " | " | " | " | 129–131 |
| 96 | " | $CH_2$–$CH_2$ | $OCH_3$ | " | " | " | " | ½$C_4H_4O_4$ | 217–219 |
| 97 | " | " | $OC_4H_9$ | " | " | " | " | $C_4H_4O_4$ | 206–208 |

-continued

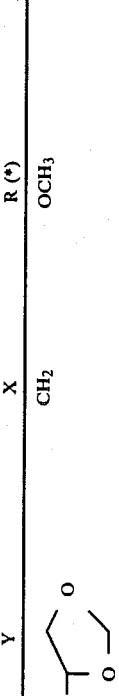

| NO. | Y | X | R (*) | R₁ | R₂ | R₃ | Method Example | Base/Salt form | m.p. °C. |
|---|---|---|---|---|---|---|---|---|---|
| 98 | (1,3-dioxolane) | CH₂ | OCH₃ | | | | | " | 179–181 |
| 99 | " | " | OC₂H₅ | " | " | " | " | " | 198–200 |
| 100 | " | " | OC₃H₇ | " | " | " | 1 | " | 189–191 |
| 101 | " | " | OC₄H₉ | " | " | " | " | " | 180–182 |
| 102 | " | " | OCH₃ | " | NO₂ | " | 2 | Base | 214–216 |
| 103 | (methyl-dioxolane) | " | " | " | Cl | " | 1 | C₄H₄O₄ | 177–179 |
| 104 | (dimethyl-dioxolane) | " | " | " | " | " | " | Base | 171–173 |
| 105 | (1,3-dioxane) | " | OC₄H₉ | " | " | " | 2 | C₄H₄O₄ | 180–182 |
| 106 | " | " | OCH₃ | " | " | " | " | " | 222–224 |
| 107 | " | " | OC₂H₅ | " | " | " | 1 | " | 174–176 |
| 108 | " | " | OC₃H₇ | " | " | " | " | " | 186–188 |
| 109 | " | " | OC₄H₉ | " | " | " | " | " | 198–200 |
| 110 | " | " | OC₅H₁₁ | " | " | " | " | C₄H₄O₄ | 188–190 |
| 111 | " | " | OC₆H₁₃ | " | " | " | " | " | 191–193 |
| 112 | " | " | OCH₃ | " | NO₂ | " | " | Base | 218–220 |
| 113 | " | " | OC₂H₅ | 4-N(CH₃)₂ | Cl | " | " | C₄H₄O₄ | 149–151 |
| 114 | " | CH₂—CH₂ | OCH₃ | 4-NH₂ | " | " | 2 | " | 223–225 |

-continued

Structure:

R₂–[benzene with R₁, R(*), CONH-]–[piperidine with R₃, N–X–Y]

| NO. | Y | X | R (*) | R₁ | R₂ | R₃ | Method Example | Base/Salt form | m.p. °C |
|---|---|---|---|---|---|---|---|---|---|
| 115 | [1,3-dioxepane] | CH₂ | " | " | " | " | " | " | 205–207 |
| 116 | [1,3-dioxepane] | " | OC₄H₉ | " | " | " | " | " | 178–180 |
| 117 | [dioxepene] | " | OCH₃ | " | " | " | " | " | 204–206 |
| 118 | [dioxepene] | " | OC₄H₉ | " | " | " | " | " | 178–180 |
| 119 | [spiro-bis-dioxane] | " | OCH₃ | " | " | " | " | C₄H₄O₄ | 212–214 |
| 120 | [tetrahydrofuran-CH₂-dioxane] | " | OC₄H₉ | " | " | " | " | " | 150–152 |
| 121 | [tetrahydrofuran-CH₂-dioxane] | " | OCH₃ | " | " | " | 1 | Base | 170–173 |
| 122 | " | " | OC₃H₇ | " | " | " | " | " | 114–116 |
| 123 | " | " | OC₄H₉ | " | NO₂ | " | " | " | 94–96 |
| 124 | " | " | OCH₃ | " | " | " | 1 | Base | 222–224 |
| 125 | [methoxy-tetrahydrofuran] | " | OCH₃ | " | Cl | H | " | C₄H₄O₄ | 173–175 |
| 126 | " | " | OC₂H₅ | " | " | " | " | " | 189–191 |
| 127 | " | " | OC₃H₇ | " | " | " | " | " | 172–174 |
| 128 | " | " | OC₄H₉ | " | " | " | " | Base | 113–115 |

-continued
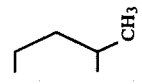
| NO. | Y | X | R (*) | R₁ | R₂ | R₃ | Method Example | Base/Salt form | m.p. °C. |
|---|---|---|---|---|---|---|---|---|---|
| 129 |  | " | OCH₃ | " | " | " | " | C₄H₄O₄ | 208–210 |
| 130 | " | " | OC₂H₅ | " | " | " | " | " | 163–165 |
| 131 | " | " | OC₃H₇ | " | " | " | " | " | 159–161 |
| 132 | " | " | OC₄H₉ | " | " | " | " | " | 186–188 |
| 133 | " | " | OCH₃ | " | NO₂ | " | " | Base | 212–214 |
| 134 | " | " | OCH₃ | " | Cl | " | " | C₄H₄O₄ | 201–203 |
| 135 | 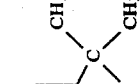 | " | OC₂H₅ | " | " | " | " | " | 218–220 |
| 136 | " | " | OC₃H₇ | " | " | " | " | " | 205–207 |
| 137 | " | " | OC₄H₉ | " | " | " | " | " | 186–188 |
| 138 | " | " | OCH₃ | " | NO₂ | " | " | Base | 231–233 |
| 139 | | " | " | " | Cl | " | 2 | C₄H₄O₄ | 163–165 |
| 140 | | " | OC₄H₉ | " | " | " | " | " | 176–178 |
| 141 |  | " | OCH₃ | " | " | " | " | Base | 191–193 |
| 142 | " | " | OC₄H₉ | " | " | " | " | " | 132–134 |
(*) Straight-chain if not indicated
(**) Fumaric acid

EXAMPLE 3

A solution of N-[1-[2-(1,3-dioxolanyl)methyl]piperid-4-yl]-2-butoxy-4-amino-5-chlorobenzamide (2 g; 0.005 moles) and methyl iodide (1.25 ml; 0.02 moles) in chloroform (60 ml.) was stirred at room temperature overnight. The precipitated solid was recovered by filtration and washed with acetone and diethyl ether to yield 1.8 g. of N-[1-[2-(1,3-dioxolanyl)methyl]piperid-4-yl]-2-butoxy-4-amino-5-chlorobenzamide methyl iodide, m.p. 215°–217° C.

By a similar procedure the following compound was prepared:

N-[1-[2-(1,3-dioxolanyl)methyl]piperid-4-yl]-2-hexoxy-4-amino-5-chlorobenzamide methyl iodide, m.p. 188°–190° C.

The following Examples illustrate pharmaceutical compositions according to the present invention and procedures for their preparation.

EXAMPLE 4

50,000 Tablets each containing 1 mg of N-[1-[2-(1,3-dioxolanyl)methyl]-piperid-4-yl]-2-butoxy-4-amino-5-chlorobenzamide were prepared from the following formulation:

| | |
|---|---|
| N—[1-[2-(1,3-dioxolanyl)methyl]-piperid-4-yl]-2-butoxy-4-amino-5-chlorobenzamide | 50 g |
| microcrystalline cellulose | 950 g |
| lactose spray dried | 4950 g |
| carboxymethyl starch | 200 g |
| sodium stearyl fumarate | 50 g |
| colloidal silicon dioxide | 50 g |

Procedure

All the powders were passed through a screen with aperture of 0.6 mm, then mixed in a suitable mixer for 20 minutes and compressed into 125 mg tablets using 6 mm discs and flat bevelled punches. The distintegration time of the tablets was about 60 seconds.

EXAMPLE 5

2,000 Bottles (125 ml volume) each containing a solution of 25 mg of N-[1-[2-(1,3-dioxolanyl)methyl]-piperid-4-yl]-2-butoxy-4-amino-5-chlorobenzamide were prepared as follows:

| | |
|---|---|
| N—[1-[2-(1,3-dioxolanyl)methyl]-piperid-4-yl]-2-butoxy-4-amino-5-chlorobenzamide | 50 g |
| sorbitol | 120000 g |
| sorbic acid | 250 g |
| citric acid | 250 g |
| distilled water q.s. | 250 liters |
| flavouring agent | q.s. |

Procedure

The N-[1-[2-(1,3-dioxolanyl)methyl]-piperid-4-yl]-2-butoxy-4-amino-5-chlorobenzamide and the sorbic acid were dissolved in 150 liters of water and then the sorbitol, citric acid and flavouring agent were added with stirring until dissolution. The mixture was diluted to 250 liters and filled into 125 ml bottles using an appropriate filling machine.

EXAMPLE 6

10,000 Ampoules each containing 0.5 mg of N-[1-[2-(1,3-dioxolanyl)methyl]-piperid-4-yl]-2-butoxy-4-amino-5-chlorobenzamide were prepared from the following formulation:

| | |
|---|---|
| N—[1-[2-(1,3-dioxolanyl)methyl]-piperid-4-yl]-2-butoxy-4-amino-5-chlorobenzamide | 5 g |
| sodium chloride | 250 g |
| lactic acid | 5 g |
| N Sodium hydroxide aqueous solution | q.s. to pH = 4 |
| Water injectable grade q.s. | 50 liters |

Procedure

The N-[1-[2-(1,3-dioxolanyl)methyl]-piperid-4-yl]-2-butoxy-4-amino-5-chlorobenzamide, the lactic acid and the sodium chloride were dissolved in 40 liters of water. The resulting solution was neutralized to pH=4 with the sodium hydroxide solution, diluted to 50 liters, then passed through a bacteria-retaining filter and filled under sterile conditions into 5 ml glass ampoules in known manner.

EXAMPLE 7

5,000 Suppositories each containing 1 mg of N-[1-[2-(1,3-dioxolanyl)methyl]-piperid-4-yl]-2-butoxy-4-amino-5-chlorobenzamide were prepared as follows:

| | |
|---|---|
| N—[1-[2-(1,3-dioxolanyl)methyl]-piperid-4-yl]-2-butoxy-4-amino-5-chlorobenzamide | 5 g |
| theobroma oil | 9995 g |

Procedure

The theobroma oil was melted and the active compound suspended in it. The mixture was then poured into appropriate suppository moulds to make 2.0 g suppositories.

EXAMPLE 8

100,000 Capsules each containing 1 mg of N-[1-2-(1,3-dioxolanyl)methyl]-piperid-4-yl]-2-butoxy-4-amino-chlorobenzamide were prepared as follows:

| | |
|---|---|
| N—[1-[2-(1,3-dioxolanyl)methyl]-piperid-4-yl]-2-butoxy-4-aminochlorobenzamide | 100 g |
| lactose | 10500 g |
| corn starch | 9000 g |
| colloidal silicon dioxide | 200 g |
| magnesium stearate | 200 g |

Procedure

All the powders, previously passed through a screen with an opening of 0.6 mm, were mixed for 20 minutes and distributed into 100,000 capsules of appropriate size using a filling machine.

EXAMPLE 9

8.000 supositories each containing 10 mg of N-[1-[2-(1,3-dioxolanyl)methyl]piperid-4-yl]-2-butoxy-4-amino-5-chlorobenzamide-were prepared as follows:

| | |
|---|---|
| N—[1-[2-(1,3-dioxolanyl)methyl]piperid-4-yl]-2-butoxy-4-amino-5-chlorobenzamide | 80 g. |
| Theobroma oil | 15920 g. |

Procedure

The theobroma oil was melted and the active compound suspended in it. The mixture was then poured

We claim:
1. A compound of the formula I:

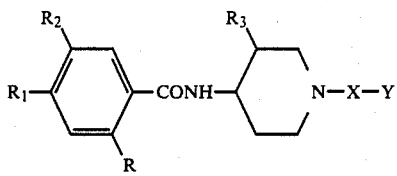

in which:
R represents an alkoxy, alkenyloxy or alkynyloxy group, each group containing up to 7 carbon atoms,
$R_1$ is hydrogen or a $NR_4R_5$, or $NR_6COR_7$ group, where $R_4$, $R_5$ and $R_6$, which may be the same or different, is each hydrogen or an alkyl containing one to four carbon atoms and $R_7$ is an alkyl containing one to four carbon atoms or trifluoromethyl group,
$R_2$ is hydrogen, halogen, or a nitro, or sulphamoyl group,
$R_3$ represents hydrogen or a methyl or methoxy group,
X represents a straight or branched chain polyalkylene containing up to 4 carbon atoms, a non-terminal carbon of which may optionally be replaced by an oxygen atom, and
Y represents a non-aromatic cyclic ether or a non-aromatic cyclic thioether group, said cyclic ether or thioether containing from 5 to 8 ring atoms, containing at least one ring oxygen or ring sulfur atom, and pharmaceutically acceptable salts thereof.

2. A compound according to claim 1 wherein Y is a cyclic ether group.

3. A compound according to claim 1 wherein Y is a mononuclear ring system containing 5–8 ring atoms of which 1 or 2 are ring O and/or S atoms and the remainder are carbon.

4. A compound according to claim 1 wherein Y includes two ring O or S atoms in non-adjacent positions in the ring.

5. A compound according to claim 1 wherein Y comprises a cyclic ether or cyclic thioether in which adjacent ring carbon atoms may together form part of a further non-aromatic ring containing 5 to 7 ring atoms comprising carbon and up to 2 additional hetero atoms selected from oxygen and sulphur, provided that when 2 additional hetero atoms are present, said additional hetero atoms are in non-adjacent positions in the further ring.

6. A compound according to claim 5 wherein the further ring system is a cyclic ether or cyclic thioether.

7. A compound according to claim 1 wherein a cyclic ether or cyclic thioether is directly bonded to group X.

8. A compound according to claim 1 wherein Y is or includes a 1,3-dioxolan-2-yl, 1,3-dioxolan-4-yl, 4,4,5,5-tetramethyl-1,3-dioxolan 2-yl-, 1,3-dioxan-2-yl, 1,3-dioxepanyl or tetrahydrofur-2-yl ring.

9. A compound according to claim 1 wherein X is $-CH_2-$ or $-CH_2-CH_2-CH_2-$.

10. A compound according to claim 1 wherein R is methoxy, n-propoxy or n-butoxy.

11. A compound according to claim 1 wherein $R_1$ is $NH_2$.

12. A compound according to claim 1 wherein $R_2$ is Cl.

13. A compound according to claim 1 which is N-[1-[2-(1,3-dioxolanyl)methyl]-piperid-4-yl]-2-butoxy-4-amino-5-chloro-benzamide.

14. A compound according to claim 1 which is
N-[1-[4-(1,3-dioxolanyl)methyl]-piperid-4-yl]-2-methoxy-4-amino-5-chloro-benzamide,
N-[1-[2-(1,3-dioxepanyl)methyl]-piperid-4-yl]-2-n-butoxy-4-amino-5-chloro-benzamide,
N-[1-[3-(2-tetrahydrofuryl)propyl]-piperid-4-yl]-2-n-propoxy-4-amino-5-chloro-benzamide,
N-[1-[2-(1,3-dioxanyl)methyl]-piperid-4-yl]-2-n-propoxy-4-amino-5-chloro-benzamide,
N-[1-[2-(4,4,5,5-tetramethyl-1,3-dioxolanyl)methyl]-piperid-4-yl]-2-n-butoxy-4-amino-5-chloro-benzamide or
N-[1-[2-(1,3-dioxanyl)methyl]-piperid-4-yl]-2-n-butoxy-4-amino-5-chloro benzamide.

15. A pharamceutical composition for treating gastrointestinal disorders in a mammal comprising an effective amount of compound or salt according to claim 1 together with a pharmaceutically acceptable carrier or diluent.

16. A method of combatting gastrointestinal disorders in a mammal including man which comprises administering to the mammal an effective amount of a compound according to claim 1.

17. A compound of the formula

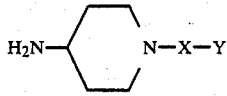

where, X and Y are as defined in claim 1.

18. A compound according to claim 17, which is 4-amino-1-[2-(1,3-dioxolanyl)methyl]-piperidine.

19. A compound according to claim 1 wherein Y comprises an cyclic ether or cyclic thioether in which at least one of the hydrogen atoms attached to at least one ring carbon atom is replaced by one or more methyl or methoxymethyl groups.

20. A compound according to claim 1 wherein Y includes one ring O or S atom.

21. A compound according to claim 1 wherein $R_4$, $R_5$ and $R_6$ which may be the same or different, is each hydrogen or a methyl group and $R_7$ is a methyl or trifluoromethyl group.

22. A compound according to claim 1 wherein Y is a monocyclic ether or a monocyclic thioether.

* * * * *